United States Patent [19]

Inden et al.

[11] Patent Number: 5,523,465
[45] Date of Patent: Jun. 4, 1996

[54] PROCESS FOR PRODUCING AN UNSYMMETRICAL DIESTER OF α, β-UNSATURATED DICARBOXYLIC ACID

[75] Inventors: Yoshimi Inden; Tadashi Yamauchi; Seiji Yamashita; Nami Ohgaya, all of Kyoto, Japan

[73] Assignee: Sanyo Chemical Industries, Ltd., Kyoto, Rep. of Korea

[21] Appl. No.: 411,933

[22] Filed: Mar. 28, 1995

[51] Int. Cl.$^6$ ..................................... C07C 29/34
[52] U.S. Cl. ............................................. 560/201
[58] Field of Search ................................. 560/201

*Primary Examiner*—José G. Dees
*Assistant Examiner*—Samuel Barts
*Attorney, Agent, or Firm*—Oblon, Spivak, McClelland, Maier & Neustadt

[57] ABSTRACT

A process for producing a colorless unsymmetrical-diester of maleic acid, useful as a raw material of an emulsifier for emulsion polymerization and as a modifier for a polymer, which comprises:

(1) reacting maleic anhydride with a monohydric alcohol in the presence of an inert organic solvent, in a molar ratio of 1:(1.0–1.2) to obtain maleic acid mono ester containing substantially no unreacted maleic anhydride, and (2) reacting said monoester with an alkenyl halide in the presence of a tertiary amine and water, in a molar ratio of said monoester:water of 1:(0.01–0.20).

24 Claims, No Drawings

PROCESS FOR PRODUCING AN UNSYMMETRICAL DIESTER OF α, β-UNSATURATED DICARBOXYLIC ACID

BACKGROUND OF THE INVENTION

1. Field of the Invention

This invention relates to a process for producing a colorless unsymmetrical diester of α,β-unsaturated dicarboxylic acid, useful as a raw material of an emulsifier for emulsion polymerization and as a modifier for a polymer.

2. Description of the Prior Art

It is well known to produce an unsymmetrical diester by reacting a dicarboxylic acid anhydride with a monohydric alcohol to obtain a monoester, and then reacting it with an alkyl halogenide in the presence of a tertiary amine.

But, an unsymmetrical diester of an α,β-unsaturated dicarboxylic acid produced by above-mentioned process, is remarkable of a color development. The diester is got color through a reaction of the monoester with the alkyl halogenide.

SUMMARY OF THE INVENTION

It is an object of the present invention to provide a process capable of providing a colorless unsymmetrical diester of an α,β-unsaturated dicarboxylic acid with high purity.

Briefly, the object of this invention as hereinafter will become more readily apparent having been attained broadly by providing a process for producing a colorless unsymmetrical diester of an α,β-unsaturated dicarboxylic acid, which comprises:

(1) reacting an α,β-unsaturated dicarboxylic acid anhydride (a1) with a monohydric alcohol (a2), in the presence of an inert organic solvent, in a molar ratio of (a1):(a2) of 1:(1.0–1.2) to obtain an α,β-unsaturated dicarboxylic acid mono ester(A), containing substantially no unreacted α,β-unsaturated dicarboxylic acid anhydride, and (2) reacting (A) with an alkenyl halide (B) in the presence of a tertiary amine (C) and water in a molar ratio of (A):water of 1:(0.01–0.20).

DETAILED DESCRIPTION OF THE PREFERRED EMBODIMENTS

Suitable examples of an α,β-unsaturated dicarboxylic acid anhydride (a1) include maleic anhydride and citraconic anhydride. Preferred is maleic anhydride.

Suitable examples of a monohydric alcohol (a2) include $C_{1-22}$ aliphatic alcohols, including saturated ones (such as methanol, butanol, octanol, decyl alcohol, lauryl alcohol, tridecyl alcohol, tetradecyl alcohol and stearyl alcohol), and $C_{8-22}$ alkenyl alcohol (such as oleyl alcohol, 1-octene-3-ol and 7-decene-1-ol); $C_{7-22}$ aromatic alcohols (such as benzyl alcohol and 1-phenyl ethyl alcohol); and mono or polyoxyalkylene (for example oxyethylene and oxypropylene) ether of $C_{1-22}$ aliphatic alcohol, $C_{7-22}$ aromatic alcohol, phenol and $C_{7-22}$ alkyl phenol (such as nonyl phenol and dodecyl phenol). Among these, preferred are $C_{8-22}$ aliphatic alcohols.

A molar ratio of (a1):(a2) is generally 1:(1.0–1.2), preferably 1:(1.0–1.10), more preferably 1:(1.0–1.05). (a2) less than 1.0 results in color development.

During the process of reacting (a1) with (a2) to obtain (A), containing substantially no unreacted (a1), an inert organic solvent is used to minimize an unreacted (a1) by bringing sublimed (a1) back to a reactor, by a vapor of said solvent. The inert organic solvent means a solvent unreactive with (a1) and (a2). Said solvent has a boiling point generally in the range of 40°–220° C. at normal pressure.

Suitable examples of the inert organic solvent include aromatic hydrocarbons (such as benzene, toluene and xylene), aliphatic hydrocarbons (such as hexane and heptane), hydrogenated hydrocarbons (such as chloroform and 1,2-dichloroethane), ethers (such as tetrahydrofuran and dioxane) and a mixture thereof. Benzene, toluene, xylene and hexane are preferred.

An amount of said solvent is generally in the range of 1–30%, preferably 5–20% by weight, based on a total amount of (a1) and (a2).

(A) contains unreacted (a1) generally less than 0.6%, preferably 0.3% by weight, based on (A).

A reaction temperature is generally in the range of 40°–120° C., preferably 50°–100° C.

Suitable examples of an alkenyl halide (B) include vinyl halides, allyl halides, methallyl halides and oleyl halides. Allyl chloride or methallyl chloride is preferred.

Suitable examples of a tertiary amine (C) include tri $C_{1-22}$ alkyl (such as triethyl and tri-n-propyl), aryl (such as triphenyl), aralkyl (such as tribenzyl) and alkenyl (such as triallyl) amine. Among these, triethyl amine or tri-n-propyl amine is preferred.

A molar ratio of (A):(B) is generally 1:(1.0–1.3), preferably 1:(1.0–1.2), and (A):water is generally 1:(0.01–0.20), preferably 1:(0.01–0.05). (B) less than 1.0 causes poor purity, (C) less than 0.7 results in poor yield, and water less than 0.01 causes remarkably color developement, over 0.20 results in poor yeild of said diester, because of carrying out a hydrolysis of (A).

A molar ratio of (A):(C) is generally 1:(0.7–1.5), preferably 1:(0.9–1.3).

Water may be one formed through neutralization of (A) with small amount of an alkali (such as sodium hydroxide and potassium hydroxide).

The reaction of (A) with (B) in the presence of (C) and water to obtain said diester, can be carried out with or without an organic solvent. In case the reaction is carried out with the organic solvent, illustrative examples of the organic solvent include the same as used at producing (A).

A reaction temperature of (A) with (B) is generally in the range of 40°–130° C., preferably in the range of 60°–100° C.

After the reaction of (A) with (B) in the presence of (C), the product can be purified to isolate the diester, for example, by rinsing it with water or an acidic aqueous solution (such as 10% hydrochloric acid) to remove (C), mineral salt and by-product, followed by distilling off the organic solvent.

It is better to provide a colorless said diester of high purity, that isolated purified said diester is further treated with an adsorbent (D).

Suitable examples of (D) include activated charcoal, silica-alumina, activated alumina, synthetic zeolites, silica gel, acid clay and activated clay. Illustrative examples of (D) include activated charcoal powder (produced by WAKO JUNYAKU Ind. Ltd.), silica-alumina powder (produced by SYOKUBAI KASEI Ind. Ltd. ) and KYOWARD #500 (produced by KYOWA CHEMICAL Ind. Ltd. ). Among these, preferred are activated chacoal and silica-alumina.

An amount of (D) is generally in the range of 0.1–10.0%, preferably 0.5–2.0% by weight based on said diester.

3

Having generally described the invention, a more complete understanding can be obtained by reference to certain specific examples, which are included for purpose of illustration only and are not intended to be limiting unless otherwise specified.

In the following examples, part, parts and % mean part by weight, parts by weight and % by weight, respectively.

Measuring methods and conditions are as follows:
(1) Color:
   Gardner Color (ASTM D154)
(2) Unreacted $\alpha,\beta$-unsaturated dicarboxylic acid content and purity measurement with gel permeation chromatography:
   Equipment: HLC-8020, produced by Toyo Soda Manuf.
   Columns: TSK gel G4000HXL, G3000HXL and G2000HXL produced by Toyo Soda Manuf.
   Temperature: 40° C.
   Sample solution: 0.5% tetrahydrofuran solution.
   Amount of solution: 100 microlitters.
   Detector: Refractometer.
Content and purity were estimated from areas of charts.

EXAMPLE 1

Into an autoclave, were charged 295 parts of maleic anhydride, 570 parts of lauryl alcohol and 85 parts of toluene. The mixture was reacted at 60° C. for 5 hours under sealed condition, to obtain maleic acid monolauryl ester, containing 0.2% unreacted maleic anhydride. After adding to the mixture, 5 parts of sodium hydroxide, 275 parts of allyl chloride and 375 parts of triethyl amine, an atmosphere was substituted with nitrogen. The mixture was reacted at 80° C. for 8 hours, and cooled to a room temperature. The mixture was rinsed with 90 parts of 10% hydrochloric acid aqueous solution, followed by distillation of toluene under vacuum, to obtain 965 parts of lauryl allyl maleate of 98.6% purity and of Gardner Color 3. A molar ratio of maleic anhydride:lauryl alcohol was 1:1.02, and maleic acid monolauryl ester:allyl chloride:triethyl amine:formed water was 1:1.19:1.23:0.04.

EXAMPLE 2

In the same manner as Example 1 except using 575 parts of lauryl alcohol, 90 parts of xylene, 355 parts of methallyl chloride and 530 parts of tri-n-propyl amine, in place of 570 parts of lauryl alcohol, 90 parts of toluene, 275 parts of allyl chloride and 375 parts of triethyl amine, was obtained 1,000 parts of lauryl methallyl maleate of 98.6% purity and of Gardner Color 3. A molar ratio of maleic anhydride:lauryl alcohol was 1:1.03, and maleic acid monolauryl ester:methallyl chloride: tri-n-propyl amine:formed water was 1:1.30:1.23:0.04.

Example 3

In the same manner as Example 1 except using 600 parts of tridecyl alcohol, 2.2 parts of water, 240 parts of allyl chloride and 335 parts of triethyl amine, in place of 570 parts of lauryl alcohol, 5 parts of sodium hydroxide, 275 parts of allyl chloride and 375 parts of triethyl amine, was obtained 960 parts of lauryl allyl maleate of 97.1% purity and of Gardner Color 3. A molar ratio of maleic anhydride:lauryl alcohol was 1:1, and maleic acid monolauryl ester:allyl chloride:triethyl amine:water was 1:1.05:1.10:0.04.

EXAMPLE 4

In the same manner as Example 1 except using 865 parts of stearyl alcohol, 90 parts of hexane, 7 parts of sodium hydroxide, 250 parts of allyl chloride and 560 parts of tri-n-propyl amine, in place of 570 parts of lauryl alcohol, 90 parts of toluene, 275 parts of allyl chloride and 375 parts of triethyl amine, was obtained 1,200 parts of stearyl allyl maleate of 97.6% purity and of Gardner Color 3. A molar ratio of maleic anhydride:stearyl alcohol was 1:1.07, and maleic acid monostearyl ester:allyl chloride: tri-n-propyl amine: formed water was 1:1.10:1.30:0.06.

EXAMPLE 5

In the same manner as Example 1 except using 610 parts of tridecyl alcohol, 7 parts of sodium hydroxide and 325 parts of methallyl chloride, in place of 570 parts of lauryl alcohol, 5 parts of sodium hydroxide and 275 parts of allyl chloride, was obtained 1,010 parts of tridecyl methallyl maleate of 98.6% purity and of Gardner Color 3. A molar ratio of maleic anhydride:tridecyl alcohol was 1:1.02, and maleic acid monotridecyl ester:methallyl chloride:triethyl amine:formed water was 1:1.19:1.23:0.06.

EXAMPLE 6

In the same manner as Example 1 except using 890 parts of oleyl alcohol, 300 parts of allyl chloride and 455 parts of triethyl amine, in place of 570 parts of lauryl alcohol, 275 parts of allyl chloride and 375 parts of triethyl amine, was obtained 1,200 parts of oleyl allyl maleate of 97.4% purity and of Gardner Color 4. A molar ratio of maleic anhydride:oleyl alcohol was 1:1.1, and maleic acid monooleyl ester:allyl chloride:triethyl amine:formed water was 1:1.3:1.5:0.04.

EXAMPLE 7

100 parts of lauryl allyl maleate produced in Example 1, and 1 part of a silica-alumina powder (produced by SYOKUBAI KASEI Ind. Ltd.) were mixed at 75 C. for 1 hour, followed by filtering off silica-alumina powder, to obtain 99 parts of lauryl allyl maleate of Gardner Color 1.

EXAMPLE 8

100 parts of tridecyl allyl maleate produced in Example 3, and 1 part of a silica-alumina powder (produced by SYOKUBAI KASEI Ind. Ltd.) were mixed at 75° C. for 1 hour, followed by filtering off the silica-alumina powder, to obtain 99 parts of tridecyl allyl maleate of Gardner Color less than 1.

EXAMPLE 9

100 parts of tridecyl methallyl maleate produced in Example 5, and 1 part of an activated charcoal powder (produced by WAKO JUNYAKU Ind. Ltd.) were mixed at 75° C. for 1 hour, followed by filtering off the activated charcoal, to obtain 99 parts of tridecyl methallyl maleate of Gardner Color less than 1.

EXAMPLE 10

100 parts of oleyl allyl maleate produced in Example 6, and 2 parts of an activated charcoal powder (produced by WAKO JUNYAKU Ind. Ltd.) were mixed at 75° C. for 1 hour, followed by filtering off the activated charcoal, to obtain 98 parts of oleyl allyl maleate of Gardner Color less than 1.

Comparative Example 1

Into an autoclave, were charged 295 parts of maleic anhydride and 560 parts of lauryl alcohol. The mixture was reacted at 60° C. for 5 hours under sealed condition, to obtain maleic acid monolauryl ester, containing 1.3% unreacted maleic anhydride. After adding to the mixture, 275 parts of allyl chloride and 375 parts of triethyl amine, an atmosphere was substituted with nitrogen. The mixture was reacted at 80° C. for 8 hours, and cooled to a room temperature. The mixture was rinsed by 90 parts of 10% hydrochloric acid aqueous solution, to obtain 960 parts of lauryl allyl maleate of 92.7% purity and of Gardner Color more than 10. A molar ratio of maleic anhydride:lauryl alcohol was 1:1, and maleic acid monolauryl ester:allyl chloride:triethyl amine was 1:1.19:1.23.

Comparative Example 2

In the same manner as Comparative Example 1 except using 300 parts of maleic anhydride and 600 parts of tridecyl alcohol, in place of 295 parts of maleic anhydride and 570 parts of lauryl alcohol, respectively, was obtained 985 parts of tridecyl allyl maleate of 93.0% purity and of Gardner Color more than 10. Maleic acid mono tridecyl ester contained 1.0% unreacted maleic anhydride. A molar ratio of maleic anhydride:tridecyl alcohol was 1:0.98, and maleic acid mono tridecyl ester:allyl chloride:triethyl amine was 1:1.19:1.23.

Comparative Example 3

Into an autoclave, were charged 295 parts of maleic anhydride and 825 parts of stearyl alcohol. A mixture was reacted at 60° C. for 5 hours under sealed condition, to obtain maleic acid monostearyl ester, containing 1.5% unreacted maleic anhydride. After adding to the mixture, 11.2 parts of toluene, 275 parts of allyl chloride and 530 parts of tri-n-propyl amine, an atmosphere was substituted with nitrogen. The mixture was reacted at 80° C. for 8 hours, and cooled to a room temperature. The mixture was rinsed by 90 parts of 10% hydrochloric acid aqueous solution, followed by distillation of toluene, to obtain 1,200 parts of stearyl allyl maleate of 94.5% purity and of Gardner Color 9. A molar ratio of maleic anhydride:stearyl alcohol was 1:1.02, and maleic acid monostearyl ester:allyl chloride:tri-n-propyl amine was 1:1.19:1.23.

Comparative Example 4

100 parts of lauryl allyl maleate produced by Comparative Example 1, and 10 parts of silica-alumina powder (produced by SYOKUBAI KASEI Ind. Ltd.) were mixed at 75° C. for 1 hour, followed by filtering off silica-alumina powder, to obtain 90 parts of lauryl allyl maleate of Gardner Color 8.

As shown in Example 1–6, the unsymmetrical diesters of $\alpha,\beta$-unsaturated dicarboxylic acid produced by the process of the invention, were colorless, while those of Comparative Examples 1–3 were severely colored, and therefore are useful as a law material of an emulsifier for emulsion polymerization and as a modifier for a polymer. Moreover as shown in Example 7–10, said diester treated with an adsorbent were perfectly colorless. On the other side, as shown in Comparative Example 4, lauryl allyl maleate, produced in Comperative Example 3, treated with adsorbent 10 times as Examples was still colored.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for producing an unsymmetrical diester of an $\alpha,\beta$-unsaturated dicarboxylic acid, which comprises:

(1) reacting an $\alpha,\beta$-unsaturated dicarboxylic acid anhydride (a1) with a monohydric alcohol (a2) in the presence of an inert organic solvent, in a molar ratio of (a1):(a2) in the range of 1:(1.0–1.2) to obtain an $\alpha,\beta$-unsaturated dicarboxylic mono ester(A), containing substantially no unreacted $\alpha,\beta$-unsaturated dicarboxylic acid anhydride, and (2) reacting (A) with an alkenyl halide (B) in the presence of a tertiary amine (C) and water, in a molar ratio of (A):water of 1:(0.01–0.20).

2. The process of claim 1, wherein (a1) is maleic anhydride.

3. The process of claim 1, wherein (a2) is at least one compound selected from the group consisting of $C_{1-22}$ aliphatic alcohols, $C_{7-22}$ aromatic alcohols, and oxyalkylene ethers of $C_{1-22}$ aliphatic alcohols, $C_{7-22}$ aromatic alcohols, phenols or $C_{7-22}$ alkyl phenols.

4. The process of claim 1, wherein (a2) is at least one compound selected from the group consisting of $C_{8-22}$ saturated aliphatic alcohols and $C_{8-22}$ alkenyl alcohols.

5. The process of claim 1, wherein (B) is allyl chloride or methallyl chloride.

6. The process of claim 1, wherein (C) is a tri $C_{1-22}$ alkyl, aryl, aralkyl or alkenyl amine.

7. The process of claim 1, wherein (C) is triethyl amine or tri-n-propyl amine.

8. The process of claim 1, wherein a molar ratio of (a1):(a2) is in the range of 1:(1.0–1.05).

9. The process of claim 1, wherein a molar ratio of (A):(B) is in the range of 1:(1.0–1.2).

10. The process of claim 1, wherein a molar ratio of (A):(C) is in the range of 1:(0.7–1.5).

11. The process of claim 1, wherein a molar ratio of (A):water is in the range of 1:(0.01–0.05).

12. A process for producing an unsymmetrical diester of $\alpha,\beta$-unsaturated dicarboxylic acid, which comprises (1) reacting an $\alpha,\beta$-unsaturated dicarboxylic acid anhydride (a1) with a monohydric alcohol (a2), in the presence of an inert organic solvent, in a molar ratio of (a1):(a2) in the range of 1:(1.0–1.2) to obtain an $\alpha,\beta$-unsaturated dicarboxylic acid mono ester(A), containing substantially no unreacted $\alpha,\beta$-unsaturated dicarboxylic acid anhydride, (2) reacting (A) with an alkenyl halide (B) in the presence of a tertiary amine (C) and water in a molar ratio of (A):water of 1:(0.01–0.20), (3) removing the tertiary amine from the reaction product; and (4) treating the product with an adsorbent(D).

13. The process of claim 12, wherein (a1) is maleic anhydride.

14. The process of claim 12, wherein (a2) is at least one compound selected from the group consisting of $C_{1-22}$ aliphatic alcohols, $C_{7-22}$ aromatic alcohols, and oxyalkylene ethers of $C_{1-22}$ aliphatic alcohols, $C_{7-22}$ aromatic alcohols, phenol or $C_{7-22}$ alkyl phenol.

15. The process of claim 12, wherein (B) is allyl chloride or methallyl chloride.

16. The process of claim 12, wherein (C) is a tri $C_{1-22}$ alkyl, aryl, aralkyl or alkenyl amine.

17. The process of claim 12, wherein a molar ratio of (a1):(a2) is in the range of 1:(1.0–1.05).

18. The process of claim 12, wherein a molar ratio of (A):(B) is in the range of 1:(1.0–1.2).

19. The process of claim 12, wherein a molar ratio of (A):(C) is in the range of 1:(0.7–1.5).

20. The process of claim 12, wherein the molar ratio of (A):water is in the range or 1:(0.01–0.05).

21. The process or claim 12, wherein (D) is selected from the group consisting of activated charcoal, silica-alumina, activated alumina, synthetic zeolites, silica gel, acid clay and activated clay.

22. The process or claim 12, wherein (D) is activated charcoal.

23. The process of claim 12, wherein (D) is silica-almina.

24. The process of claim 12, wherein (D) is used in an amount of 0.1–10.0% by weight based on said diester.

* * * * *

UNITED STATES PATENT AND TRADEMARK OFFICE
CERTIFICATE OF CORRECTION

PATENT NO. : 5,523,465
DATED : June 4, 1996
INVENTOR(S) : Yoshimi INDEN, ET AL.

It is certified that error appears in the above-indentified patent and that said Letters Patent is hereby corrected as shown below:

On the title page, Item [73], the Assignee's address, should read:

-- [73] Kyoto, JAPAN. --

Signed and Sealed this

Twenty-fourth Day of September, 1996

Attest:

BRUCE LEHMAN

Attesting Officer

Commissioner of Patents and Trademarks